United States Patent [19]

Shoesmith

[11] Patent Number: Plant 5,935

[45] Date of Patent: Apr. 7, 1987

[54] CHRYSANTHEMUM PLANT NAMED LOBO

[75] Inventor: May V. Shoesmith, Westfield, England

[73] Assignee: Ball Pan Am Plant Company, Parrish, Fla.

[21] Appl. No.: 746,799

[22] Filed: Jun. 20, 1985

[51] Int. Cl.[4] ..... A01H 5/00

[52] U.S. Cl. ..... Plt./77

[58] Field of Search ..... Plt./77

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Lobo having flat capitulum form and decorative capitulum type; bright white ray florets on outside rows, with mature center florets being creamy yellow; uniform eight week flowering response using photoperiodic control and natural flowering date of October 8 in the midwest and October 31 in Florida when grown as a garden variety; diameter across inflorescence is 1" to 2", and height is 6" to 8" above edge of a 4" pot when grown photoperiodically and 1' to 2' high when grown as a garden variety.

1 Drawing Figure

The present invention comprises a new and distinct cultivar of *Chrysanthemum morifolium,* Ramat., hereinafter referred to by the cultivar name Lobo.

Lobo is a product of a planned breeding program which had the objective of creating new garden Chrysanthemum cultivars with compact cushion habit, white decorative flowers, and with the ability to be grown year around in 4" pots. Such traits in combination were not present or needed improvement in previously available commercial cultivars.

Lobo was originated from a hybridization made by May Victoria Shoesmith in a controlled breeding program in Westfield, Woking, England in 1977. The male and female parents are unknown at this time.

Lobo was discovered and selected as one flowering plant within the progeny of the stated parentage by or under the supervision of May Victoria Shoesmith in 1978 in a controlled environment in West Chicago, Ill., and given the code #FG-78-308-WS.

The first act of asexual reproduction of Lobo was accomplished when vegetative cuttings were taken from the initial selection in February of 1979 in a controlled environment in West Chicago, Ill. by a technician working under formulations established and supervised by May Victoria Shoesmith. Horticultural examination of selected units initiated February of 1979 has demonstrated that the combination of characteristics as herein disclosed for Lobo are firmly fixed and are retained through successive generations of asexual reproduction.

Lobo has not been observed under all possible environmental conditions. The phenotype may vary significantly with variations in environment such as temperature, light intensity and day length. The following observations, measurements and comparisons describe plants grown in West Chicago, Ill. under greenhouse and field conditions which approximate those generally used in commercial practice.

The following traits have been repeatedly observed and are determined to be basic characteristics of Lobo which in combination distinguish this Chrysanthemum as a new and distinct cultivar:

(1) Flat capitulum form.

(2) Decorative capitulum type.

(3) Bright white ray florets on the outside rows; center ray florets are creamy white; disc florets show through as lime green, but turn yellow as they age.

(4) Diameter across face of flower is 1" to 2".

(5) Can be grown as a garden variety or under greenhouse conditions.

(6) Uniform 8 week flowering response using photoperiodic control; natural flowering date is approximately October 8 in the midwest and October 31 in Florida.

(7) Height is 6" to 8" above the edge of a 4" pot; height varies depending on number of long days prior to bud initiation, maturity of cuttings, and temperature. In the garden, the plant forms a compact cushion of 1' to 2' high.

Of the many commercial cultivars known to the present inventor, the most similar in comparison to Lobo is Baby Tears. In comparison to Baby Tears, Lobo has an 8 week flowering response when grown in a 4" pot using photoperiodic control, is more vigorous and does not pink as much. The flower type and plant habit are similar to those same characteristics of Baby Tears.

The accompanying photographic drawing shows typical inflorescence and foliage characteristics of Lobo. The photograph is in black and white except for a cluster of flowers in which the creamy white center ray florets appear.

In the following description, color references are made to The Royal Horticultural Society Colour Chart. The color values were determined at approximately 12:00 noon on May 2, 1985 under inflorescent light at Bradenton, Fla.

Classification:

*Botanical.*—*Chrysanthemum morifolium,* Ramat., cv Lobo.

*Commercial.*—Garden and greenhouse mum.

INFLORESCENCE

A. Capitulum:

*Form.*—Flat.

*Type.*—Decorative.

*Diameter across face.*—0.75" to 1.5".

B. Corolla of ray florets:

*Color (general tonality from a distance of three meters).*—White.

*Color (upper surface).*—155D, center 154A, maturing to a creamy white.

*Color (under surface).*—155D.

Corolla of disc florets:

*Color (mature).*—Yellow.

*Color (immature).*—Green.

D. Reproductive organs:

*Androecium.*—Present in disc florets only; insignificant.

*Gynoecium.*—One per both ray and disc floret.

PLANT

A. General appearance:

*Height.*—1′ to 1.5′ when grown outside in natural season conditions; 6″ above edge of 4″ pot using photoperiodic control.

B. Foliage:

*Color (upper surface).*—147A.

*Color (under surface).*—147B.

*Shape.*—Deeply lobed, margin repand.

I claim:

1. A new and distinct cultivar of Chrysanthemum plant named Lobo, as described and illustrated, and particularly characterized by its flat capitulum form and decorative capitulum type; bright white ray florets on outside rows, with mature center florets being creamy yellow; uniform eight week flowering response using photoperiodic control, and natural flowering date of October 8 in the midwest and October 31 in Florida when grown as a garden variety; diameter across inflorescence is 1″ to 2″, and height is 6″ to 8″ above edge of a 4″ pot when grown photoperiodically and 1′ to 2′ high when grown as a garden variety.

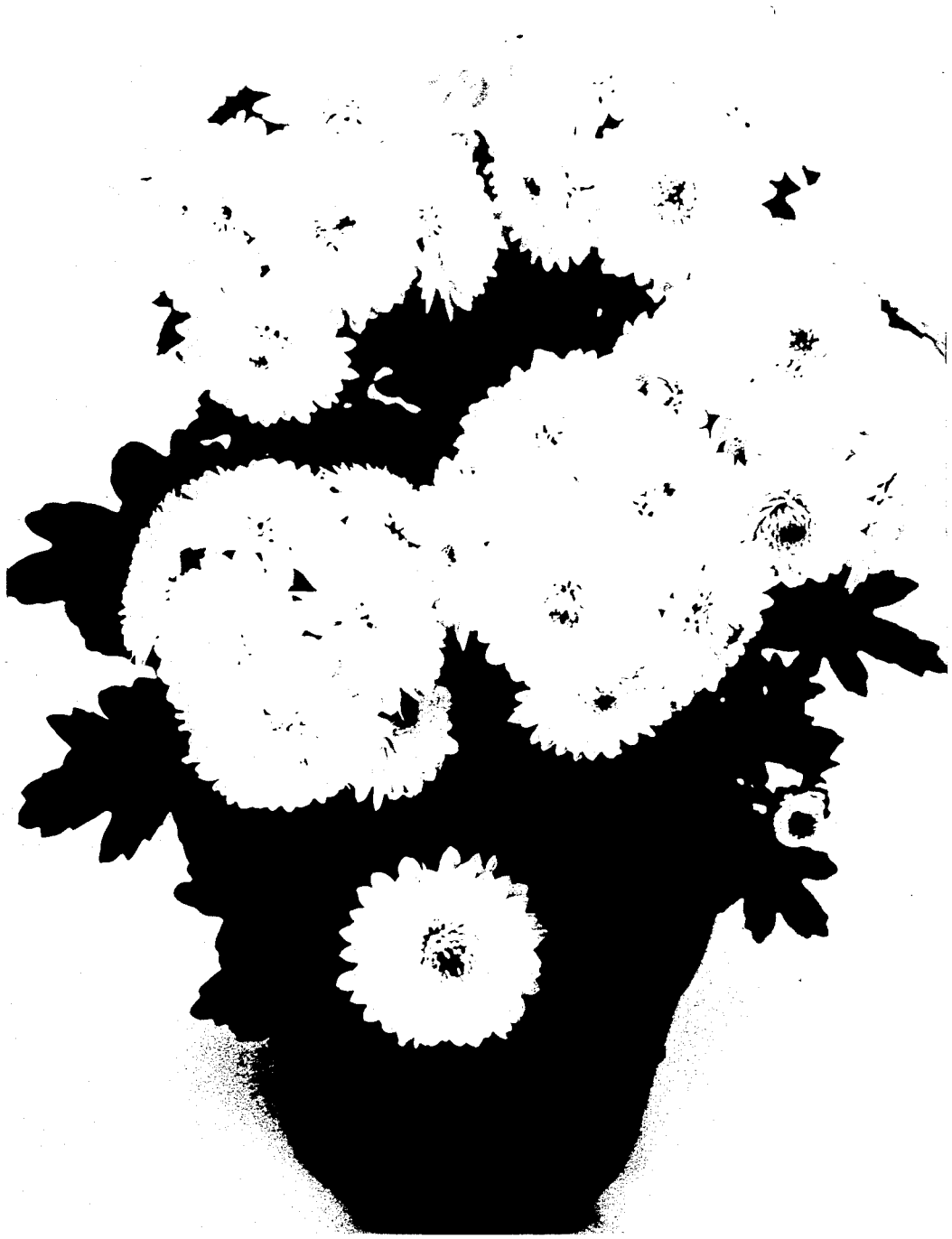

* * * * *